US008211022B2

(12) United States Patent
Lo et al.

(10) Patent No.: US 8,211,022 B2
(45) Date of Patent: Jul. 3, 2012

(54) SYSTEMS AND METHODS FOR ASSESSING DYNAMIC CEREBRAL AUTOREGULATION

(75) Inventors: Men-Tzung Lo, Jhongli (TW); Yanhui Liu, Mountain View, CA (US)

(73) Assignee: DynaDx Corporation, Mountain View, CA (US)

(*) Notice: Subject to any disclaimer, the term of this patent is extended or adjusted under 35 U.S.C. 154(b) by 853 days.

(21) Appl. No.: 12/273,386

(22) Filed: Nov. 18, 2008

(65) Prior Publication Data

US 2010/0125213 A1   May 20, 2010

(51) Int. Cl.
  *A61B 8/00* (2006.01)
  *A61B 8/14* (2006.01)
  *A61B 6/00* (2006.01)

(52) U.S. Cl. ........ 600/454; 600/202; 600/381; 600/382; 600/451; 600/453; 600/456; 600/462; 600/465; 600/468; 600/480; 600/481; 600/485; 600/501; 702/66; 702/67; 702/72; 702/77; 702/194

(58) Field of Classification Search ............ 600/202, 600/386, 453, 454, 455, 462, 465, 468, 480, 600/485, 501, 381, 382, 451, 456, 481; 702/194, 702/66, 67, 72, 77
See application file for complete search history.

(56) References Cited

U.S. PATENT DOCUMENTS 5,579,774 A   12/1996   Miller
6,738,734 B1 *  5/2004   Huang .................... 702/194

OTHER PUBLICATIONS

Lo et al. Multimodal Pressure Flow Analysis: Application of Hilbert Huang Transform in Cerebral Blood Blow Regulation, EURASIP J Adv Signal Process. 2008: 785243—pp. 1-25: (PMC Aug. 21, 2008).*

Iwasaki et al. Acute exposure to normobaric mild hypoxia alters dynamic relationships between blood pressure and cerebral blood flow at very low frequency (Journal of Cerebral Blood Flow & Metabolism 27: 776-784 (2007).*

Reinhard et al. Transfer function analysis for clinical evaluationof dynamic cerebral autoregulation—a comparison between spontaneous and respiratory-induced oscillations. Physiol. Meas 24: 27-43 (2003).*

Reinhard et al. Dynamic cerebral autoregulation in Acute Ischemic Stroke Assessed From Spontaneous Blood Pressure Fluctuations. Stroke 36: 1684-1689 (2005).*

Panerai et al. Multiple Coherence of cerebral blood flow in humans. Am J. Physiol. Heart Circ. Physiol. 291: H251-H259 (2006).*

Liau et al. Dynamic cerebral autoregulation assessment using chaotic analysis in diabetic autonomic neuropathy. Med. Bio. Comput 46: 1-9 (2008).*

(Continued)

*Primary Examiner* — Gail R Gabel
(74) *Attorney, Agent, or Firm* — SV Patent Service

(57) ABSTRACT

A method for dynamic cerebral autoregulation (CA) assessment includes acquiring a blood pressure (BP) signal having a first oscillatory pattern from a first individual, acquiring a blood flow velocity (BFV) signal having a second oscillatory pattern from the first individual, decomposing the BP signal into a first group of intrinsic mode functions (IMFs), decomposing the BFV signal into a second group of IMFs, determining dominant oscillatory frequencies in the first group of IMFs, automatically selecting a first characteristic IMF from the first group of IMFs that has its associated dominant oscillatory frequency in a predetermined frequency range, automatically selecting a second characteristic IMF from the second group of IMFs, calculating a time sequence of instantaneous phase difference between the first characteristic IMF and the second characteristic IMF, computing an average of the instantaneous phase difference in the time sequence, and identifying a pathological condition in the first individual.

20 Claims, 6 Drawing Sheets

OTHER PUBLICATIONS

Reinhard et al. Cerebral dysautoregulation and the risk of ischemic events in occlusive carotid artery disease. J Neurol. 255: 1182-1189 (2008).*

Ogawa et al. Dexmedetomidine Weakes Dynamic Cerebral Autoregulation as Assessedt by Transfer Function Analysis and the Thigh Cuff Method. Anaesthesiology 109: 642-650 (2008).*

* cited by examiner

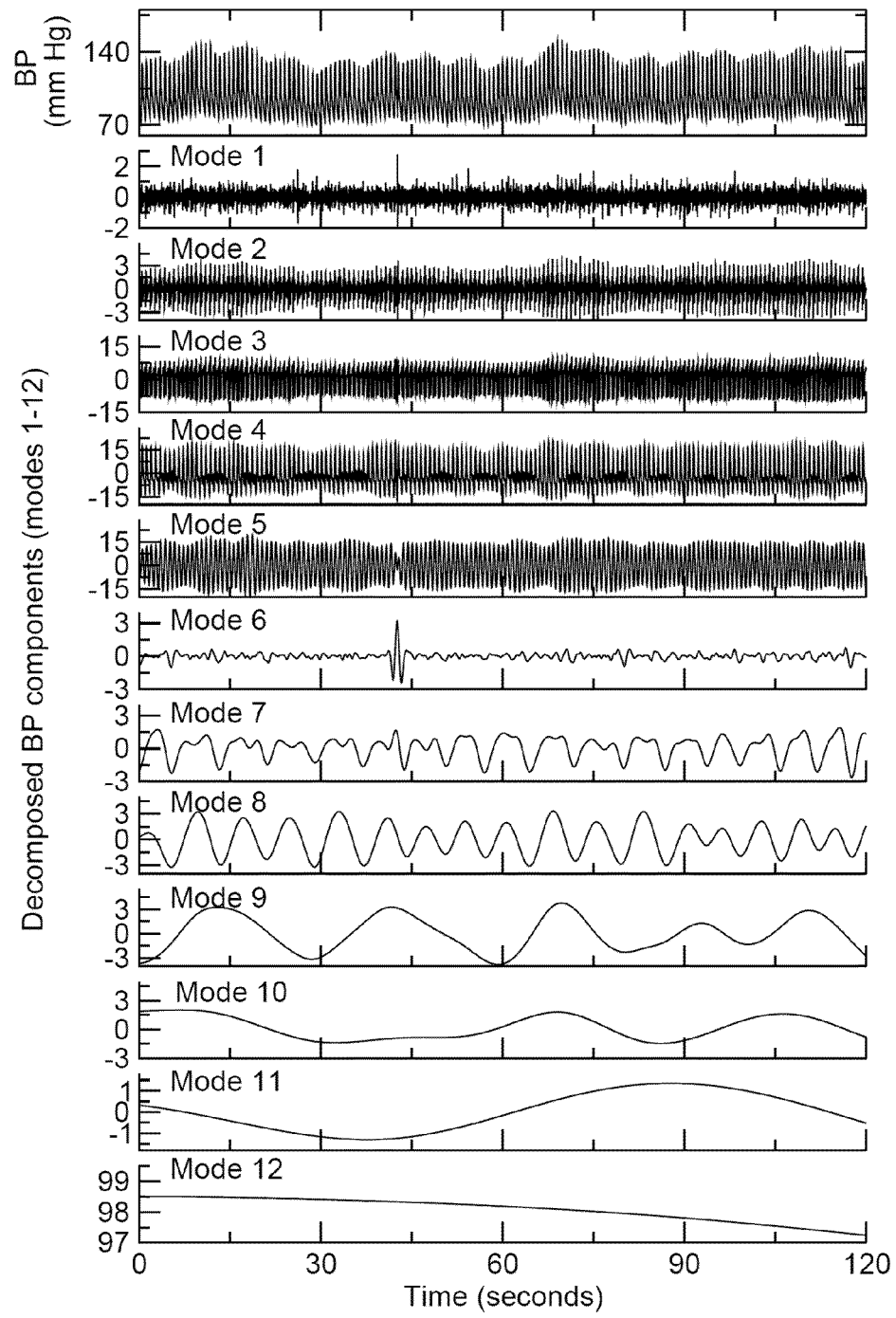

SYSTEMS AND METHODS FOR ASSESSING DYNAMIC CEREBRAL AUTOREGULATION

BACKGROUND

The present disclosure relates generally to assessment of dynamic cerebral autoregulation, specifically, the assessment of dynamic cerebral autoregulation function by analyzing multiple physiological signals.

Cerebral autoregulatory mechanisms are engaged in compensating for metabolic demands and perfusion pressure variations under physiologic and pathologic conditions.

Cerebral microvasculature controls perfusion using myogenic and neurogenic regulation by adjusting small-vessel resistances in response to beat-to-beat blood pressure (BP) fluctuations. Dynamic cerebral autoregulation (CA) reflects the ability of the cerebral microvasculature to control perfusion. Some conventional CA assessment techniques (such as transfer function technique) normally simulate cerebral regulation by linear and time-invariant mathematical models, which treat blood pressure variation as input and cerebral blood flow as output. The relationship between BP and cerebral blood flow velocity (BFV) is explored by a transfer function. The gain and phase shifts between power spectra of BP and BFV are calculated. Alterations in BP-BFV relationship under pathologic conditions can be identified by the transfer function.

A major drawback of some conventional CA assessment techniques is that the analysis is based on Fourier transform that is limited to superimposed sinusoidal signals with constant amplitudes and periods. Conventional CA assessment techniques often cannot accurately analyze non-stationary BP and BFV signals used in clinical diagnosis. Providing accurate, reliable, and noninvasive assessment of dynamic cerebral autoregulation continues to be a challenge in medical diagnostics.

SUMMARY

In a general aspect, the present invention relates to a method for dynamic cerebral autoregulation assessment. The method includes acquiring a blood pressure signal having a first oscillatory pattern from a first individual; acquiring a blood flow velocity signal having a second oscillatory pattern from the first individual; decomposing the BP signal into a first group of intrinsic mode functions (IMFs); decomposing the BFV signal into a second group of IMFs; determining dominant oscillatory frequencies in the first group of IMFs; automatically selecting a first characteristic IMF from the first group of IMFs that has its associated dominant oscillatory frequency in a predetermined frequency range; automatically selecting a second characteristic IMF from the second group of IMFs; calculating a time sequence of instantaneous phase difference between the first characteristic IMF and the second characteristic IMF; computing an average of the instantaneous phase difference in the time sequence; and identifying a pathological condition in the first individual if the average of the instantaneous phase difference satisfies a predetermined criterion.

In another general aspect, the present invention relates to a computer program product comprising a computer useable medium having computer readable program code functions embedded in said medium for causing a computer to acquire a blood pressure signal having a first oscillatory pattern from a first individual; acquire a blood flow velocity signal having a second oscillatory pattern from the first individual; decompose the BP signal into a first group of IMFs; decompose the BFV signal into a second group of IMFs; determine dominant oscillatory frequencies in the first group of intrinsic mode functions; automatically select a first characteristic IMF from the first group of IMFs that has its associated dominant oscillatory frequency in a predetermined frequency range; automatically select a second characteristic IMF from the second group of IMFs; calculate a time sequence of instantaneous phase difference between the first characteristic IMF and the second characteristic IMF; compute an average of the instantaneous phase difference in the time sequence; and identify a pathological condition if the average of the instantaneous phase difference satisfies a predetermined criterion.

In another general aspect, the present invention relates to a system for dynamic cerebral autoregulation assessment. The system includes a first probe that can acquire a first physiological signal having a first oscillatory pattern from a first individual; a second probe that can acquire a second physiological signal having a second oscillatory pattern from the first individual; and an analyzer that can decompose the first physiological signal into a first group of intrinsic mode functions, decompose the second physiological signal into a second group of IMFs, select a first characteristic IMF from the first group of IMFs, select a second characteristic IMF from the second group of IMFs, calculate a time sequence of instantaneous phase difference between the first characteristic IMF and the second characteristic IMF; and identify a pathological condition if an average of the instantaneous phase difference satisfies a predetermined criterion.

Implementations of the system may include one or more of the following. The BFV signals can include a BFV signal from left middle cerebral arteries (BFVL) or a BFV signal from right middle cerebral arteries (BFVR). The step of selecting a second characteristic IMF can include determining dominant oscillatory frequencies in the second group of IMFs; and selecting one of the second group of IMFs that has its associated dominant oscillatory frequency in a predetermined frequency range. At least a portion of the predetermined frequency range can be in a range from approximately 0.1 Hz to approximately 0.4 Hz. The predetermined criterion can be based on a threshold phase angle between about 30 degrees and about 50 degrees. The method further includes identifying the pathological condition if the average of the instantaneous phase difference is below the threshold phase angle. The pathological condition can include diabetes, stroke, hypertension, aging, dementia, or traumatic brain injuries (TBI). The step of decomposing the BP signal can include obtaining a first envelope of local maxima and local minima in the BP signal to obtain a first IMF; subtracting the first IMF from the BP signal in order to obtain a first residual signal; and obtaining a second envelope of local maxima and local minima in the first residual signal to obtain the second IMF in the first group of IMFs. The method can further include conducting a Valsalva maneuver, a head-up tilt, or a sit-to-stand movement by the first individual before the steps of acquiring the BP signal and the BFV signal.

The described systems and methods provide more reliable and more accurate assessment for dynamic cerebral autoregulation, which enables accurate diagnosis of a wide range of pathological conditions. The disclosed methods are non-invasive, and can also be fully automated. The described systems and methods are also simpler and less expensive than some conventional techniques.

Although the invention has been particularly shown and described with reference to multiple embodiments, it will be understood by persons skilled in the relevant art that various changes in form and details can be made therein without departing from the spirit and scope of the invention.

BRIEF DESCRIPTION OF THE DRAWINGS

The following drawings, which are incorporated in and form a part of the specification, illustrate embodiments of the present invention and, together with the description, serve to explain the principles of the invention.

FIG. 4A illustrates the blood pressure waveform (of FIG. 3B) obtained from the diabetes patient.

FIG. 4B illustrates waveforms of BP intrinsic mode functions calculated from the blood pressure waveform shown in FIG. 4A.

DETAILED DESCRIPTION

Figure 1:
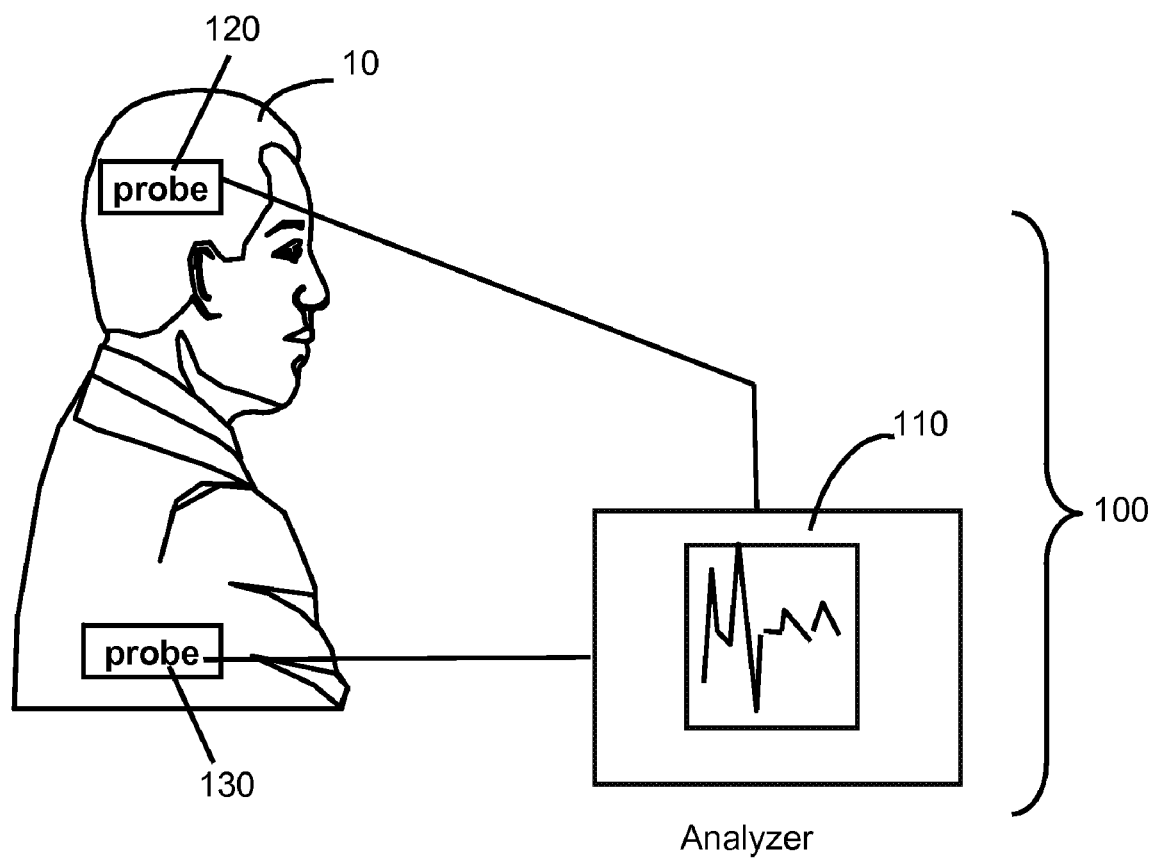
FIG. 1 is a schematic diagram illustrating a system for assessing cerebral autoregulation in accordance to the present invention.

Referring to FIG. 1, an exemplified dynamic cerebral autoregulation assessment system 100 includes an analyzer 110 and one or more probes 120, 130 that can be attached to a patient 10. The probes 120, 130 include transducers and sensors that are configured to measure physiological signals such as continuous beat-to-beat blood pressure (BP) and blood flow velocity (BFV) from the patient 10. Cerebral BFV can be measured using transcranial Doppler ultrasound (TCD) under a non-stimulated condition or during sudden systematic BP changes induced by Valsalva maneuver (VM), head-up tilt, or a sit-to-stand movement. The probes 120, 130 can send sensing signals to the analyzer 110 in response to the physiological signals. The sensing signals are often in analog form. The analyzer 110 can include an analog-to-digital (A/D) converter for digitizing the sensing signals. The analyzer 110 also includes a computer processor that is configured to process and analyze the sensing signals after they are digitized by the A/D converter. An algorithm can be pre-stored in a computer memory in the analyzer 110 for analyzing the sensing signals. The analyzer 110 can also include necessary input/output devices that allow a user to enter instructions to process the data, and a display for displaying the raw sensing signals and data calculated from the sensing signals. One or more or all the analyzing steps described below can be automated.

Figure 2:
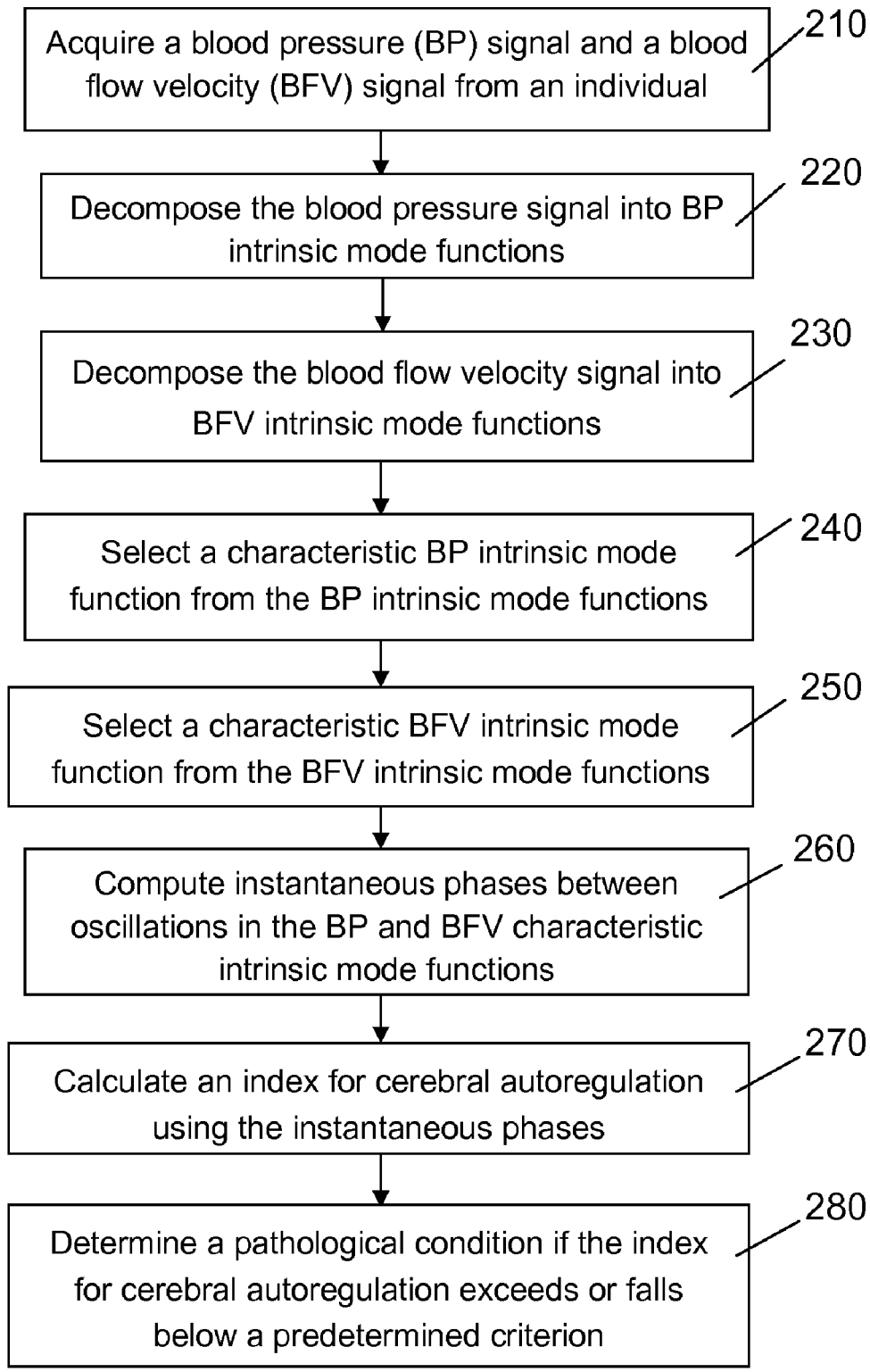
FIG. 2 is a flow diagram illustrating the steps of assessing cerebral autoregulation in accordance to the present invention.

Referring to FIG. 2, the disclosed CA assessment can include one or more of the following steps. Physiological signals are first acquired (step 210) from an individual using the CA assessment system 100 (shown in FIG. 1). The physiological signals can include BP and BFV signals. The BFV signals can include signals from left (BFVL) and right (BFVR) middle cerebral arteries (MCAs). BP, and BFVL and BFVR signals can be measured from a healthy individual, shown in FIG. 3A, can be used as a control for pathological assessment. BP, and BFVL and BFVR signals can be measured from a patient having certain pathologic conditions such as diabetes, stroke, hypertension, aging, dementia, and traumatic brain injuries (TBI). BP, and BFVL and BFVR signals obtained from a diabetes patient are shown in FIG. 3B. The physiological signals (e.g. blood pressure or blood flow) from the healthy individual (used as a control) and the patient both show oscillatory pattern related to the dynamics of respiratory oscillations.

Figure 3A:
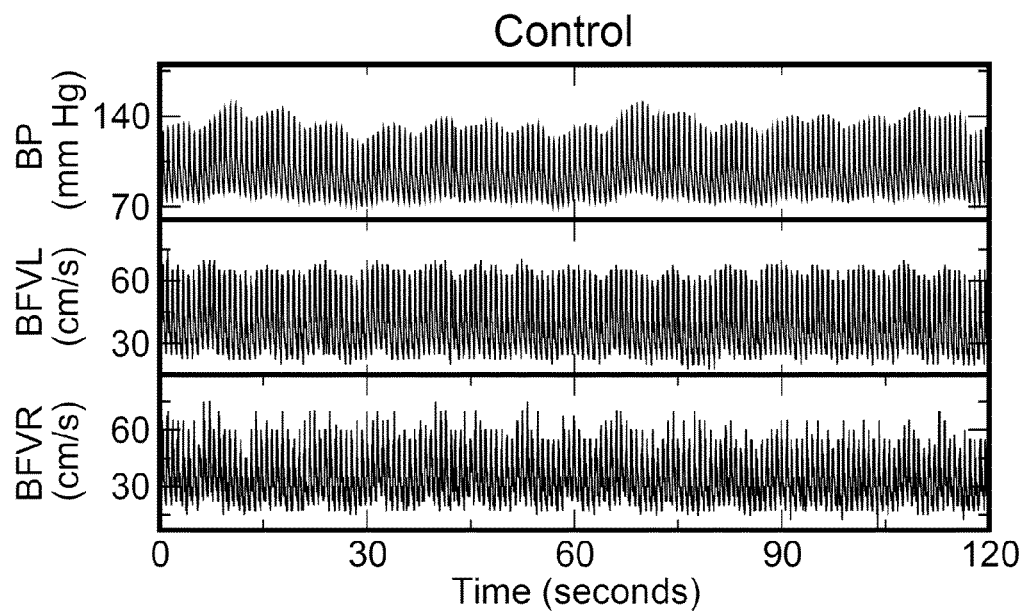
FIG. 3A illustrates exemplified waveforms of blood pressure (BP), and blood flow velocities from left (BFVL) and right (BFVR) middle cerebral arteries (MCAs) measured from a healthy individual.
Figure 3B:
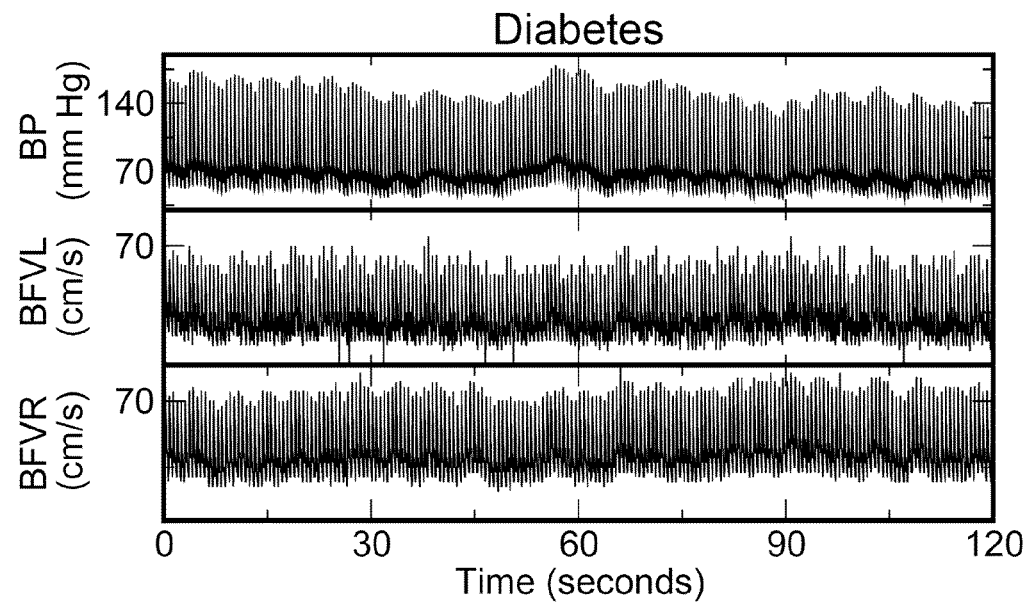
FIG. 3B illustrates exemplified waveforms of blood pressure (BP), and blood flow velocities (BFV) from left (BFVL) and right (BFVR) middle cerebral arteries measured from a diabetes patient.

The BP and BFV signals as shown in FIGS. 3A and 3B are not stationary, that is, their amplitudes and frequencies vary over time. To analytically describe such non-stationary oscillations, amplitudes and phases (or frequency) need to be characterized at any instantaneous moment. Conventional Fourier transforms, however, cannot accurately describe non-stationary signals because these signals are non-periodic.

In the present application, physiological signals can be decomposed into intrinsic mode functions (IMFs) by the ensemble empirical mode decomposition technique. The blood pressure signals from both the healthy individual and the diabetes patient are decomposed into BP IMFs (step 220). For example, the blood pressure waveform obtained from the diabetes patient shown in FIGS. 3B and 4A is decomposed into a plurality of BP intrinsic modes (e.g. Mode 1 to Mode 12), as shown in FIG. 4B. Mode 1 is obtained by tracing the envelope of local maxima and local minima in the blood pressure waveform. Mode 1 is then subtracted from the blood pressure waveform to obtain a first residual signal. Mode 2 is obtained by tracing the envelope of the maxima and minima in the first residual signal. Mode 2 is then subtracted from the first residual signal to obtain a second residual signal. Mode 3 is similarly calculated from the second residual signal. The above described decomposition steps are repeated to compute Mode 4 to Mode 12 of the BP IMFs. The decomposition algorithm generally results in decreased oscillation frequencies from Mode 1 to Mode 12 in the intrinsic mode functions. The oscillation frequencies of the successive IMFs approximately decrease by a factor of two. For control purpose, BP IMFs are also obtained from the blood pressure waveform (shown in FIG. 3A) of a healthy individual.

Similarly, IMFs can be obtained by decomposing the BFVL and BFVR signals (shown in FIG. 3A) obtained from the health individual. IMFs can be obtained by decomposing the BFVL and BFVR signals (shown in FIG. 3B) measured from the diabetes patient (step 230).

The intrinsic mode functions (BP, BFVL, or BFVR) are usually characterized by frequency-amplitude modulation in a narrow frequency band. Physiological or pathological processes are known to be associated with certain specific frequency ranges. For instance, spontaneous breathing oscillations normally exist in a frequency range of 0.1~0.4 Hz under baseline (non-stimulated) condition and in a frequency range of 0.1~0.03 Hz for oscillations induced by Valsalva maneuver.

Figure 5A:
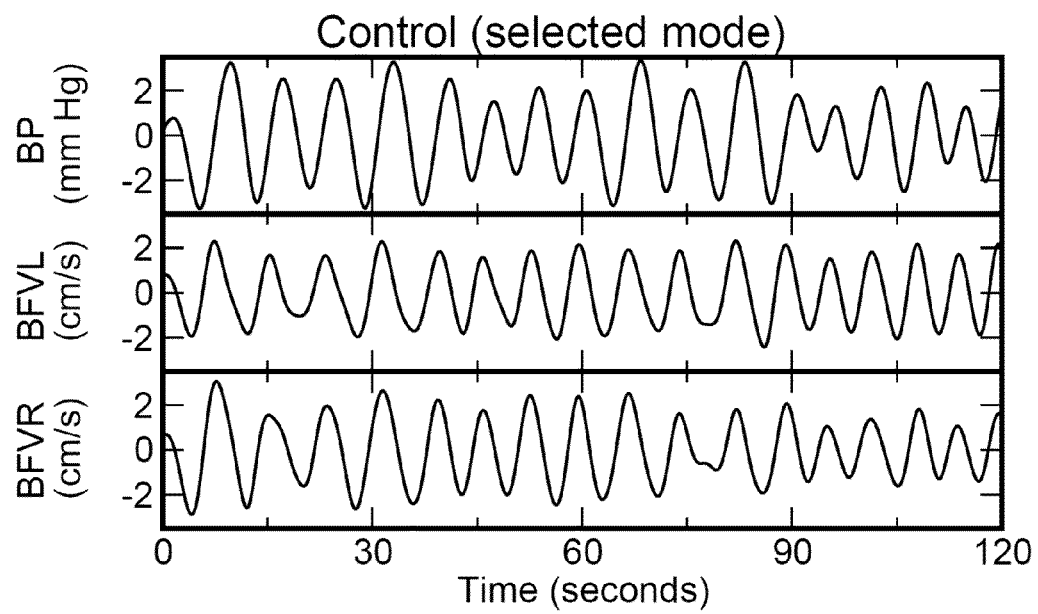
FIG. 5A illustrates waveform of a characteristic BP intrinsic mode function and characteristic BFVL and BFVR intrinsic mode functions selected from the BP, BFVL, BFVR (shown in FIG. 3A) from the healthy individual.
Figure 5B:
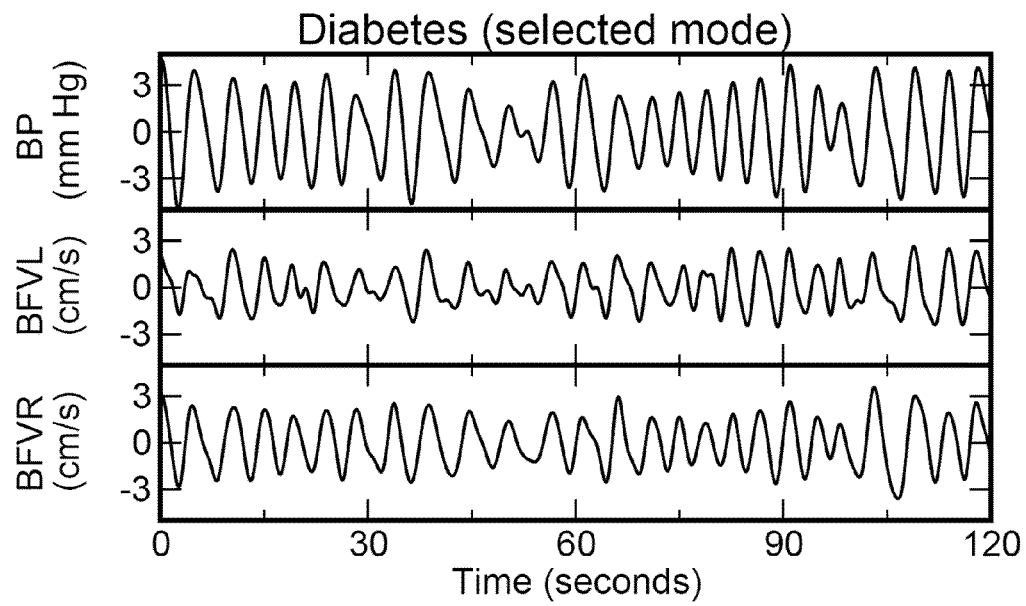
FIG. 5B illustrates waveform of a characteristic BP intrinsic mode function and characteristic BFVL and BFVR intrinsic mode functions selected from the BP, BFVL, BFVR (shown in FIG. 3B) from the diabetes patient.

A characteristic BP, BFVL or BFVR IMF having characteristic frequency in the interesting frequency range can be selected for CA assessment (step 240). For example, Mode 6 in FIG. 4B is selected from the plurality of BP IMFs for the healthy individual is shown in FIG. 5A (the upper plot). Likewise, Mode 6 is selected from the plurality of BP IMFs for the diabetes patient is shown in FIG. 5B (the upper plot). The selection of characteristic BP, BFVL or BFVR IMFs can be fully automated by determining the dominant oscillation frequencies in the IMFs. For baseline (non-stimulated) conditions, the IMFs that has characteristic frequencies between 0.1 Hz and 0.4 Hz can be automatically selected for CA assessment.

Similarly, characteristic BFVL and BFVR IMFs having their respective characteristic frequencies in a predetermined frequency range can be selected from their respective BFVL and BFVR IMFs for the healthy individual and diabetes patient (step 250). The selected characteristic BP, BFVL and BFVR IMFs from the healthy individual are jointly illustrated in FIG. 5A. The selected characteristic BP, BFVL and BFVR IMFs from the diabetes patient are jointly illustrated in FIG. 5B. As shown in FIGS. 5A and 5B, the characteristic BP, BFVL and BFVR IMFs oscillations from the healthy individual and the diabetes patient both show oscillatory patterns. But the oscillatory patterns from the diabetes patient appear to be more irregular compared to the oscillatory patterns from the healthy individual. Close scrutinizations of BP and FV signals in FIGS. 5A and 5B can reveal that the BFVL or BFVR signals have significant phase shifts behind the BP signals for a healthy individual (FIG. 5A), whereas the BFVL or BFVR signals are much more synchronized to the BP signals for the diabetes patient. It is known in the medical diagnostics that pathologic impairments of dynamic cerebral autoregulation can significantly reduce this phase shift between BP and BFV.

Figure 6A:
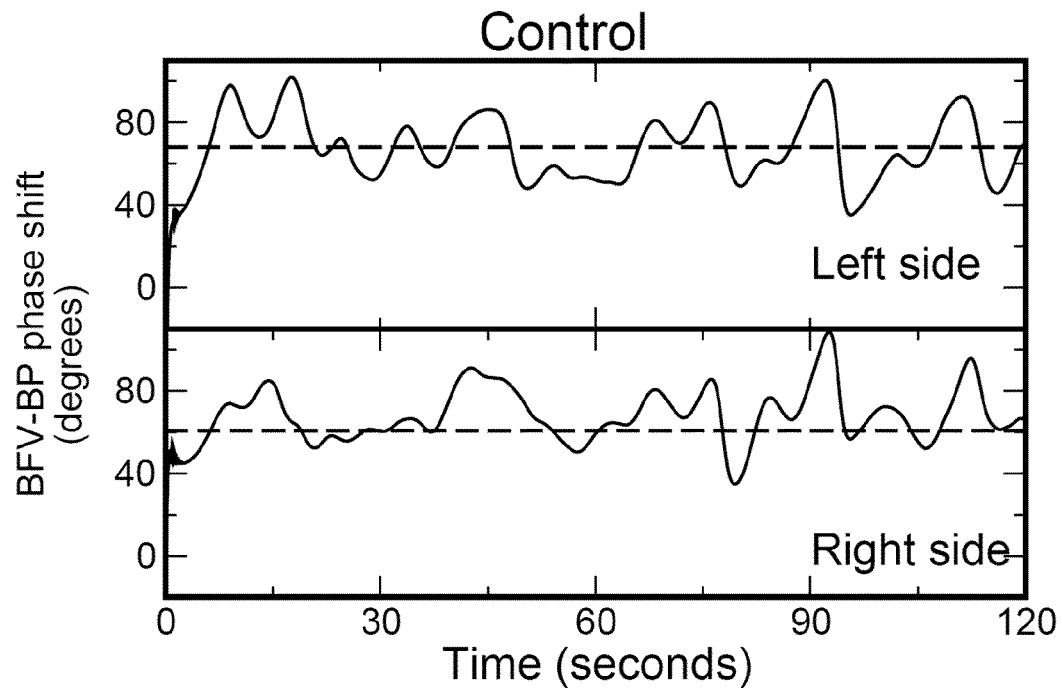
FIG. 6A illustrates waveforms of instantaneous BP-BFVL and BP-BFVR phase differences computed using the characteristic BP intrinsic mode function and characteristic BFVL and BFVR intrinsic mode functions (shown in FIG. 5A) for the healthy individual.
Figure 6B:
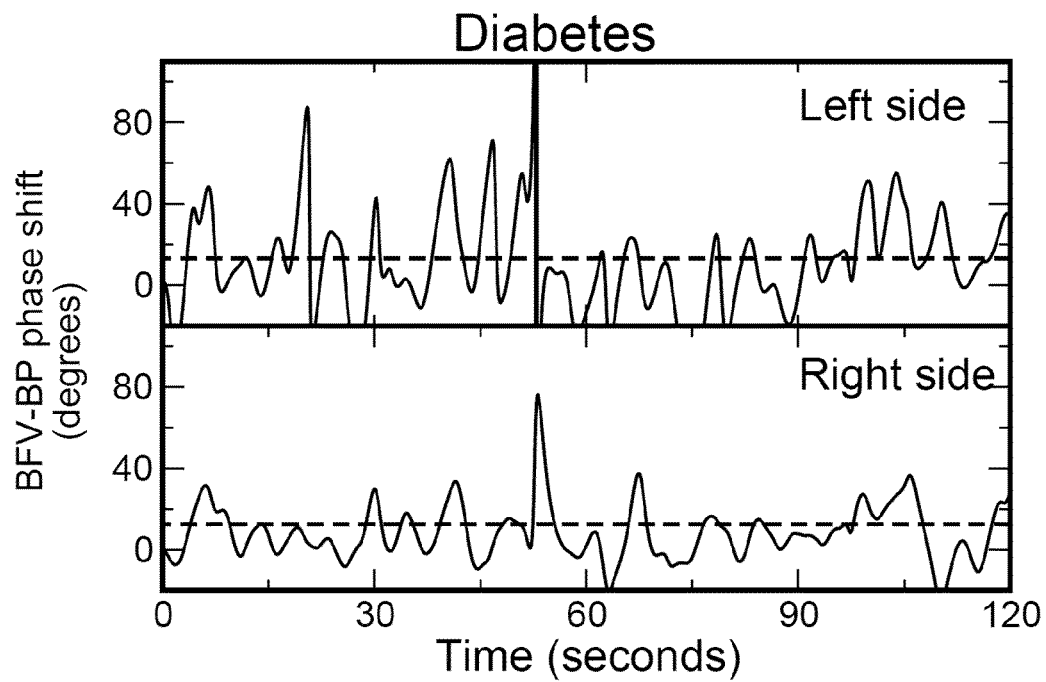
FIG. 6B illustrates waveforms of instantaneous BP-BFVL and BP-BFVR phase differences computed using the characteristic BP intrinsic mode function and characteristic BFVL and BFVR intrinsic mode functions (shown in FIG. 5A) for the diabetes patient.

Next, instantaneous phases between oscillations in the BP and BFV characteristic IMFs are computed (step 260). For the healthy individual, the instantaneous phases are separately calculated between characteristic BP and BFVL IMFs (FIG. 6A, upper plot) and between characteristic BP and BFVR IMFs (FIG. 6A, lower plot). For the diabetes patient, the instantaneous phases are also calculated between characteristic BP and BFVL IMFs (FIG. 6B, upper plot) and between characteristic BP and BFVR IMFs (FIG. 6B, lower plot).

Next, indices or "bio-markers" for CA are derived from the instantaneous phases of BP and BFV oscillations (step 270). It is known that CA typically lead to faster recovery in BFV in response to BP fluctuations for normal control subject, however, the phases of BFV oscillations follow BP oscillations more closely for patients under pathological conditions compared to healthy individuals. In other words, the BFV oscillations have smaller phase shift behind the BP oscillations for these pathological conditions. Referring to FIG. 6A, average BFV-BP phase shifts are in the range of 60-70 degrees for the healthy individual. In contrast, referring to FIG. 6B, average BFV-BP phase shifts for the diabetes patient are between approximately 10-20 degrees, which are significantly lower than the phase shifts for healthy individuals.

Average BFVL-BP and BFVR-BP phases can thus be used as indices or "bio-markers" for CA assessment. A pathological condition such as diabetes can be determined if the computed BFVL-BP or BFVR-BP phase is below a pre-determined threshold (step 280). For example, in the examples shown in FIG. 3A through FIG. 6B, diabetes condition can be determined in association with a patient if the computed average of the BFVL-BP or BFVR-BP phases is below 30, 40, or 50 degrees. Other suitable indices or "bio-markers" in BFV-BP phases for CA assessment can also include standard deviations, medians, maxima, minima, and so on. In general, a pathological condition can be determined when a CA index exceeds or falls below a predetermined condition.

It should be understood that the above described systems and methods are applicable to different physiological signals and pathological conditions from the examples described above. For example, the disclosed methods and systems are suitable for pathological conditions such as diabetes, stroke, hypertension, aging, dementia, and traumatic brain injuries (TBI). The physiological signals can be measured under normal conditions or by the Valsalva maneuver. Moreover, physiological signals other than blood pressure and blood flow velocity can be suitable to disclosed systems and methods. Phase differences from three or more separate physiological signals can be used for CA assessment and pathological determination.

What is claimed is:

1. A method for dynamic cerebral autoregulation (CA) assessment, comprising:
   acquiring a blood pressure (BP) signal having a first oscillatory pattern from a first individual;
   acquiring a blood flow velocity (BFV) signal having a second oscillatory pattern from the first individual;
   decomposing the BP signal into a first group of intrinsic mode functions (IMFs);
   decomposing the BFV signal into a second group of IMFs;
   determining dominant oscillatory frequencies in the first group of IMFs;
   automatically selecting a first IMF from the first group of IMFs that has its associated dominant oscillatory frequency in a predetermined frequency range;
   automatically selecting a second IMF from the second group of IMFs;
   calculating a time sequence of instantaneous phase difference between the first IMF and the second IMF;
   computing an average of the instantaneous phase difference in the time sequence; and
   identifying a CA-related pathological condition in the first individual if the average of the instantaneous phase difference is in a predetermined phase range criterion.

2. The method of claim 1, wherein the BFV signal is a BFV signal from left middle cerebral arteries (BFVL) or a BFV signal from right middle cerebral arteries (BFVR).

3. The method of claim 1, wherein the step of selecting a second IMF comprises:
   determining dominant oscillatory frequencies in the second group of IMFs; and
   selecting one of the second group of IMFs that has its associated dominant oscillatory frequency in a predetermined frequency range.

4. The method of claim 1, wherein the predetermined frequency range comprises a frequency in a range from approximately 0.1 Hz to approximately 0.4 Hz.

5. The method of claim 1, wherein the predetermined phase range criterion is based on a threshold phase angle between about 30 degrees and about 50 degrees.

6. The method of claim 5, further comprising identifying the CA-related pathological condition if the average of the instantaneous phase difference is below the threshold phase angle.

7. The method of claim 5, wherein the CA-related pathological condition comprises diabetes, stroke, hypertension, aging, dementia, or traumatic brain injuries (TBI).

8. The method of claim 1, wherein the step of decomposing the BP signal comprises:

obtaining a first envelope of local maxima and local minima in the BP signal to obtain a first IMF;

subtracting the first IMF from the BP signal in order to obtain a first residual signal; and obtaining a second envelope of local maxima and local minima in the first residual signal to obtain the second IMF in the first group of IMFs.

9. The method of claim 1, further comprising conducting a Valsalva maneuver, a head-up tilt, or a sit-to-stand movement by the first individual before the steps of acquiring the BP signal and the BFV signal.

10. A computer program product comprising a computer useable medium having computer readable program code functions embedded in said medium for causing a computer to:

acquire a blood pressure (BP) signal having a first oscillatory pattern from a first individual;

acquire a blood flow velocity (BFV) signal having a second oscillatory pattern from the first individual;

decompose the BP signal into a first group of intrinsic mode functions (IMFs);

decompose the BFV signal into a second group of IMFs;

determine dominant oscillatory frequencies in the first group of IMFs;

automatically select a first IMF from the first group of IMFs that has its associated dominant oscillatory frequency in a predetermined frequency range;

automatically select a second IMF from the second group of IMFs;

calculate a time sequence of instantaneous phase difference between the first IMF and the second IMF;

compute an average of the instantaneous phase difference in the time sequence; and identify a CA-related pathological condition in the first individual if the average of the instantaneous phase difference is in a predetermined phase range criterion.

11. A method for dynamic cerebral autoregulation (CA) assessment, comprising:

acquiring a first physiological signal having a first oscillatory pattern from a first individual;

acquiring a second physiological signal having a second oscillatory pattern from the first individual;

decomposing the first physiological signal into a first group of intrinsic mode functions (IMFs);

decomposing the second physiological signal into a second group of IMFs;

selecting a first IMF from the first group of IMFs;

selecting a second IMF from the second group of IMFs;

calculating a time sequence of instantaneous phase difference between the first IMF and the second IMF; and identifying a CA-related pathological condition in the first individual if the average of the instantaneous phase difference is in a predetermined phase range criterion.

12. The method of claim 11, wherein the first physiological signal and the second physiological signal are selected from the group consisting of a blood pressure (BP) signal, a blood flow velocity (BFV) signal.

13. The method of claim 12, wherein the BFV signal is a BFV signal from left middle cerebral arteries (BFVL) or a BFV signal from right middle cerebral arteries (BFVR).

14. The method of claim 11, wherein the step of selecting a first IMF comprises:

determining an dominant oscillatory frequency in the first group of IMFs; and selecting one of the first group of IMFs that has its associated dominant oscillatory frequency in a predetermined frequency range.

15. The method of claim 14, wherein the predetermined frequency range comprises a frequency in a range from approximately 0.1 Hz to approximately 0.4 Hz.

16. The method of claim 11, wherein the predetermined phase range criterion is based on a threshold phase angle between about 30 degrees and about 50 degrees.

17. The method of claim 16, wherein the CA-related pathological condition is identified if the average of the instantaneous phase difference is below the threshold phase angle.

18. The method of claim 16, wherein the CA-related pathological condition comprises diabetes, stroke, hypertension, aging, dementia, or traumatic brain injuries (TBI).

19. The method of claim 11, wherein the step of decomposing the first physiological signal comprises:

obtaining an envelope of local maxima and local minima in the first physiological signal to obtain a first IMF; and subtracting the first IMF from the first physiological signal in order to obtain a second IMF in the first group of IMFs.

20. A system for dynamic cerebral autoregulation (CA) assessment, comprising:

a first probe configured to acquire a first physiological signal having a first oscillatory pattern from a first individual;

a second probe configured to acquire a second physiological signal having a second oscillatory pattern from the first individual; and an analyzer configured to decompose the first physiological signal into a first group of intrinsic mode functions (IMFs), decompose the second physiological signal into a second group of IMFs, select a first IMF from the first group of IMFs, select a second IMF from the second group of IMFs, calculate a time sequence of instantaneous phase difference between the first IMF and the second IMF, and to identify a CA-related pathological condition in the first individual if the average of the instantaneous phase difference is in a predetermined phase range criterion.

* * * * *

UNITED STATES PATENT AND TRADEMARK OFFICE
Certificate

Patent No. 8,211,022 B2                                                                      Patented: July 3, 2012

On petition requesting issuance of a certificate for correction of inventorship pursuant to 35 U.S.C. 256, it has been found that the above identified patent, through error and without any deceptive intent, improperly sets forth the inventorship.
    Accordingly, it is hereby certified that the correct inventorship of this patent is: Men-Tzung Lo, Jhongli (TW); Yanhui Liu, Mountain View, CA (US); and Kun Hu, Jhongli (TW).

Signed and Sealed this Ninth Day of September 2014.

*MARK L. SHIBUYA*
*Supervisory Patent Examiner*
*Art Unit 1678*
*Technology Center 1600*